United States Patent [19]

McCormick et al.

[11] 4,440,753

[45] Apr. 3, 1984

[54] PURIFICATION OF GLYCOPEPTIDE ANTIBIOTICS USING NON-FUNCTIONAL RESINS

[75] Inventors: Mack H. McCormick, Westlake, Oreg.; Gene M. Wild, Indianapolis, Ind.

[73] Assignee: Eli Lilly and Company, Indianapolis, Ind.

[21] Appl. No.: 358,399

[22] Filed: Mar. 15, 1982

[51] Int. Cl.³ .......................................... A61K 135/00
[52] U.S. Cl. .................................................. 424/124
[58] Field of Search ........................................ 424/124

[56] References Cited

U.S. PATENT DOCUMENTS

| | | | |
|---|---|---|---|
| 3,067,099 | 12/1962 | McCormick et al. | 167/65 |
| 3,816,618 | 6/1974 | Raun | 424/115 |
| 3,952,095 | 4/1976 | Hamill et al. | 424/118 |
| 4,064,233 | 4/1977 | Hamill et al. | 424/118 |
| 4,115,552 | 9/1978 | Hamill et al. | 424/118 |

*Primary Examiner*—Stanley J. Friedman
*Attorney, Agent, or Firm*—Ashbrook Charles W.; Dwight E. Morrison; Arthur R. Whale

[57] ABSTRACT

Purification of glycopeptide antibiotics actaplanin and vancomycin by adsorption on non-functional resins followed by elution of the antibiotic from the resin with aqueous solvents.

9 Claims, No Drawings

PURIFICATION OF GLYCOPEPTIDE ANTIBIOTICS USING NON-FUNCTIONAL RESINS

SUMMARY

This invention relates to the purification of the glycopeptide antibiotics actaplanin and vancomycin by adsorption of the antibiotic from fermentation broths or partially purified process streams onto certain non-functional resins followed by the elution of the antibiotic from the resin with aqueous solvents.

BACKGROUND OF THE INVENTION

The antibiotic actaplanin (the name given to the antibiotic complex of A-4696 factors) and methods for the production thereof are described in U.S. Pat. Nos. 3,952,095; 4,064,233; and 4,115,552. Actaplanin is described as being useful as a growth promoter in poultry and swine.

Vancomycin and a method for its preparation and isolation are described in U.S. Pat. No. 3,067,099. Both actaplanin and vancomycin are described as being useful for improving feed efficiency in ruminants. See U.S. Pat. No. 3,816,618.

Because of the interest in these antibiotics and their importance, new and more efficient methods of isolating these antibiotics from their fermentation mixtures are continually sought.

DETAILED DESCRIPTION

The present invention provides a novel process for the purification and recovery of the glycopeptide antibiotics actaplanin and vancomycin from their fermentation broths, or their partially-purified process streams, by adsorption on a non-functional resin, followed by elution of the antibiotics from the resin with aqueous solvents.

The hereindisclosed and claimed novel method of separating and purifying actaplanin has previously been disclosed, but not claimed, for use in the separation and purification of a factor of the actaplanin complex. See U.S. application Ser. No. 217,960, filed Dec. 18, 1980.

One aspect of the present invention involves the separation and purification of the antibiotic actaplanin, an antibiotic complex which is very effective for improving growth and feed efficiency in various commercially important farm animals. The harvested actaplanin fermentation broth is generally simply dried in its entirety and mixed with feed or minerals and fed to the animals. However, in some cases, the use of the actaplanin requires at least a partially purified product, as for instance in the manufacture of a bolus, for which purpose the actaplanin must be at least 50% pure.

Prior to the present invention, the partial purification of actaplanin has been accomplished in the following manner: the antibiotic activity in the actaplanin whole fermentation broth is solubilized by adjusting the pH to either a high or a low pH, with or without the addition of water-soluble polar organic solvent; the whole broth mixture is then filtered or centrifuged to remove the mycelia, the filtrate adjusted to about pH 4.0, and the organic solvent, if present, is removed at reduced pressure; the acidic aqueous broth preparation is clarified and passed over a column of low cross-linked strong acid cation exchange resin in the sodium form (e.g., Dowex 50-X2); the resin is removed from the column, adjusted to pH 10.5, the antibiotic eluted, the eluate adjusted to neutral pH and evaporated to dryness. One disadvantage of this conventional method is that a fragile resin is used and the method requires much handling of the resin. Another disadvantage is that the actaplanin antibiotic is subjected to conditions of high pH which affect stability, and the dried eluate contains a substantial amount of salt.

In the novel process of the instant invention, the ion exchange resin is replaced with a nonfunctional resin selected from the group consisting of Amberlite XAD-16, Duolite resins ES-861 and ES-865, and Diaion HP-20. With these resins a simpler, more versatile process is thereby provided, which yields a product much lower in salt content.

The non-functional resins used in the process of this invention can be generally described as macroporus copolymers of styrene and divinylbenzene. Non-functional resins are a known class of resins and information concerning these resins, their sources, and their characteristics, appear in J. *Chromotography* 201, 287–292 (1980).

The non-functional resins are characterized by pore volume (0.5–4.5 ml/g), specific surface area (200–800 $m^2/g$), pore diameter (40–1300 Å), pore size distribution and bead size distribution.

The surface area and pore volume characteristics of the resins employed in the present process are listed in the following Table I.

TABLE I
RESIN CHARACTERISTICS

| Resin | Surface area $(m^2/g)$ | Pore volume (ml/g) |
|---|---|---|
| Diaion HP-20 | 718 | 1.16 |
| Doulite ES-861 | ~500 | ~0.900 |
| Amberlite XAD-16 | 789 | 1.45 |
| Duolite ES-865 | 650–700 | 1.4–1.5 |

We have found that the resins employed in the process of this invention are unique among other closely-related non-functional resins in that they are highly effective in the purification of actaplanin and vancomycin.

The resins employed in the process are readily obtainable from commercial sources, as shown in Table II.

TABLE II

| Resins | Manufacturer |
|---|---|
| Amberlite XAD-16 | Rohm and Haas |
| Diaion HP-20 | Mitsubishi |
| Duolite ES-861, −865 | Dia-Prosim (Diamond Shamrock) |

The novel process, as applied to the purification of the antibiotic actaplanin, can be described as a combination of a series of steps, and the various steps are recited hereinafter as a convenient means for describing the best mode of the process contemplated by us at the present time. This novel process begins with the clarified acidic aqueous broth preparation obtained in the conventional manner outlined above, and comprises:

(a) passing the clarified acidic aqueous broth preparation over a non-functional resin selected from the group consisting of Diaion HP-20, Duolite ES-865, Duolite ES-861, and Amberlite XAD-16, to adsorb the actaplanin on the non-functional resin, and washing the resin with water;

(b) eluting the actaplanin from the non-functional resin using an aqueous solution of a polar organic solvent, optionally acidified; and (c) recovering the actaplanin.

In the above, the term "polar organic solvent" is intended to include methanol, ethanol, acetone, n-propyl alcohol, isopropyl alcohol, n-butyl alcohol, isobutyl alcohol, methyl ethyl ketone, acetonitrile, tetrahydrofuran, and like solvents which have appreciable water solubility or are miscible with water. The concentration of the organic solvent in water may vary. In general, a concentration of between about 3% and 50% is satisfactory.

The optional acidification (b) is suitably accomplished employing aqueous acetic, hydrochloric, sulfuric, phosphoric, and like acids.

Thus, the filtrate (filtered whole broth), which contains an organic solvent, for example acetone, is concentrated in vacuo to remove the acetone, and the resulting aqueous concentrate adjusted to a pH in the range of about pH 1.0 to about pH 7.0, suitably pH 3.0 to about pH 5.0, preferably pH 3.2. The pH adjustment is made using aqueous base, for example aqueous sodium hydroxide, sodium carbonate, potassium hydroxid, or the like.

This antibiotic activity-containing solution is passed over a bed of the non-functional resin, or the resin is added to the solution, mixed thoroughly for several minutes, and the exhausted solution removed. The resin is washed thoroughly with water. The actaplanin antibiotic is then eluted from the resin with the aqueous solution of the polar organic solvent. Eluants include aqueous solutions of those polar solvents which will elute and solubilize actaplanin. Thus, aqueous solutions of methanol, ethanol, n-propyl alcohol, isopropyl alcohol, the butyl alcohols, acetone, methyl ethyl ketone, acetonitrile, and tetrahydrofuran are all regarded as suitable. Aqueous solutions of isopropyl alcohol or methanol, optionally acidified with acetic acid or phosphoric acid are preferred. The actaplanin is then recovered from the eluate by methods known to the art, for example precipitation and evaporation.

Alternatively, the actaplanin whole broth is first filtered with the aid of filter aid (Celite 545, diatomaceous earth, Johns-Manville Corp.). The material collected on the filter, which consists of biomass and filter aid, is slurried with 50% aqueous acetone, the slurry adjusted to about pH 1.8, using aqueous acid, and the mixture filtered and the filter cake washed with 50% aqueous acetone. This acidic, aqueous acetone filtrate is then concentrated in vacuo to remove the acetone. The acetone-free solution is passed over a column containing the non-functional resin Duolite ES-865, followed by a water wash. The actaplanin is then eluted from the non-functional resin with 50% aqueous isopropyl alcohol acidified to pH 1.0 with aqueous acid. The aqueous acid can be acetic, hydrochloric, sulfuric, phosphoric, or the like. The actaplanin is then isolated from the eluate after neutralization.

Another aspect of the invention is the application of the novel process to the purification of the antibiotic vancomycin.

An aqueous solution containing the vancomycin activity is obtained from the whole fermentation broth by methods known to the art. This aqueous solution of vancomycin is then adjusted to a pH in the range of from about pH 2 to about pH 9, suitably about pH 4 to about pH 6.5, preferably pH 6.5. The adjustment is made by addition of dilute aqueous salt or acid or base solutions having a pH range of from about pH 1.0 to about pH 11.5. Examples of such solutions include aqueous ammonium acetate and aqueous ammonium hydroxide, and dilute hydrochloric acid.

The novel process then comprises:

(a) passing the aqueous solution containing vancomycin and having a pH of about pH 4 to about pH 6.5 over a non-functional resin selected from the group consisting of Diaion HP-20, Duolite ES-865, Duolite ES-861, and Amberlite XAD-16, and washing the resin with water;

(b) eluting the vancomycin from the non-functional resin using as eluant a dilute aqueous solution of a polar organic solvent, optionally acidified; and (c) recovering the vancomycin from the eluate.

In the above, the term "polar organic solvent" has the same meanings as defined hereinabove. The aqueous solution of the water-soluble organic solvent is made acidic by the addition of aqueous acetic acid, hydrochloric acid, sulfuric acid, phosphoric acid, or the like. Thus, for example a solution of 3% isopropyl alcohol in aqueous 0.05% acetic acid is used, or a solution of 3% isopropyl alcohol in aqueous 0.05% phosphoric acid, on a weight basis.

In practicing the hereindisclosed novel process, the non-functional resins preferred for use are Diaion HP-20 and Duolite ES-865.

The invention will be more fully comprehended from the information contained in the following examples which, however, are not to be considered as limiting.

EXAMPLE 1

Thirty liters of harvested actaplanin whole broth was filtered using 10% filter-aid (Celite 545, a diatomaceous earth, Johns-Manville Products Corp.), after adding an equal volume of acetone and adjusting the pH to 1.8 with hydrochloric acid. The filtrate was concentrated in vacuo to remove the acetone.

The resulting solution was adjusted to pH 3.2 with aqueous sodium hydroxide, and passed over five liters of Diaion HP-20 resin in a three-inch diameter column at 250 ml./min. The HP-20 resin had been pretreated with methanol and washed with water. After washing with five liters of water, the column was eluted successively with 21 liters of 20% aqueous methanol, 15 liters of 50% aqueous methanol, and 15 liters of 50% aqueous acetone. Four-liter fractions were taken. Some of the activity was eluted by the 20% methanol, but most of it came off with the 50% methanol. Some activity and much color were eluted by 50% acetone, which eluate was discarded. Three of the 50% methanol fractions were combined, concentrated to one-half volume and the product precipitated by the addition of 10 volumes of isopropyl alcohol. After decantation, filtration and drying, a tan product was obtained containing about 50% of the activity in the broth at 70% purity.

EXAMPLE 2

One liter of actaplanin whole broth was filtered with the aid of filter aid and washed. Approximately 30% of the activity was present in the filtrate; the remainder was present in the filter cake. The filter cake was slurried in 1600 ml. of 50% aqueous acetone solution and adjusted to pH 1.8 with aqueous hydrochloric acid. The mixture was filtered and washed. The filtrate was concentrated in vacuo to remove the acetone. The acetone-free solution was passed over a 120 ml. column of Duolite ES-865, followed by a water wash. The column was eluted with 50% aqueous isopropyl alcohol at pH 1.0 (HCl). Fifty-ml. fractions were taken. The elution was essentially quantitative with three bed-volumes of eluate. The peak fraction (No. 4) contained about two-thirds of the activity in the eluate at about 90% purity. The total eluate averaged about 60% pure.

EXAMPLE 3

Three hundred ml. of actaplanin whole broth were adjusted to pH 3.0 with sulfuric acid. This mixture was then diluted with two volumes of hot (~95° C.) water, and there were added 80 ml. of Duolite ES-865 resin, and the mixture stirred for one hour. The resin was screened out of the mixture on a 60 mesh screen and washed with water. After being transferred to a column, the resin was eluted with a mixture of 50 parts isopropyl alcohol, 50 parts water, and 4 parts concentrated hydrochloric acid. The eluate was collected until most of the color was eluted and the column effluent attained pH 1.0. The eluate contained 69% of the antibiotic activity.

EXAMPLE 4

Whole vancomycin fermentation broth was adjusted to pH 2.45 with aqueous sulfuric acid, heated to about 50° C., and filtered.

One hundred twenty-two liters of this filtered vancomycin fermentation broth, containing ca. 260 gm. of antibiotic activity, was chromatographed over 9 liters of Ionac X-236 resin in the sodium phase (a low cross-link cation exchange resin purchased from the Sybron Corp., Birmingham, N.Y.) contained in a column measuring 4.5×50 cm., using a contact time of ca. 15 minutes. After the filtered broth had passed over the resin, the resin was washed for about 8 hours with deionized water at a flow rate of 550 ml./min.

The vancomycin was eluted from the resin using as eluant a solution of 7.2 kg. of ammonium acetate and 1.9 liters of ammonium hydroxide in 93 liters of deionized water. The fractions collected were monitored for their antibiotic content by the UV absorption at 280 m$\mu$. The fractions which contained the vancomycin were adjusted to pH 6.5 with aqueous 10% hydrochloric acid as soon as they emerged from the column. The total eluate measured 65 liters in volume and contained 222 gm. of vancomycin.

(a) Preparation of Vancomycin Base by Use of a Non-Functional Group Resin

A chromatographic column, measuring 10×180 cm., and containing 7.3 liters of Diaion HP-20 resin was prepared for use by washing with methanol until all turbidity was removed, followed by washing with deionized water until all the methanol was removed.

The 65 liters of eluate obtained from the Ionac X-236 resin column, as described above, was passed downflow over the column of Diaion HP-20 resin, prepared as above, at a flow rate of 250-300 ml. per minute. After the 65 liters had passed over the resin, the column was washed with 33 liters of deionized water.

The antibiotic was eluted from the Diaion HP-20 resin using 59 liters of a solution of 3% isopropyl alcohol in aqueous 0.05% acetic acid, using a 15-minute contact time. This eluate was concentrated in vacuo to a volume of about 1200 ml., which contained 145 gm. of vancomycin activity. This material was then converted to the vancomycin free base.

(b) Preparation of Vancomycin Phosphate from a Non-Functional Group Resin Eluate by the Addition of Organic Solvent The eluate obtained from a Diaion HP-20 resin column by procedure (a) described above, wherein the eluant was an aqueous solution of 3% isopropyl alcohol and 0.05% of phosphoric acid (85%) on a weight basis, was concentrated to a volume which had an antibiotic concentration of 150 mg./ml. at pH 2.2. Fifty milliliters of this solution was stirred and there was slowly added thereto 50 ml. of ethanol. Crystals of vancomycin phosphate formed. The suspension was chilled overnight and filtered to recover the crystals. The crystals were washed on the filter successively with 25-50 ml. each of 50% aqueous ethanol, ethanol, and ethyl ether. The crystals were dried overnight in vacuo at a temperature of 38°-40° C. The product had a total phosphorus content of 3.08% and a bioassay of 1047 mcg./ml.

We claim:

1. A process for purifying a glycopeptide antibiotic selected from actaplanin or vancomycin which comprises:
   A. contacting an aqueous solution thereof with a macroporous, non-ionic styrene-divinylbenzene copolymer adsorption resin having an average pore volume of 0.5 to 4.5 ml/g, a surface area of 200 to 800 m$^2$/g, and a pore diameter of 40 to 1300 Å;
   B. separating the contacted resin from the aqueous solution;
   C. washing the resin with an aqueous solution having a pH value of about 1 to about 9, and containing about 3 to about 50% by volume of a polar organic solvent;
   D. recovering the glycopeptide from the aqueous washing solution by crystallization, concentration or decantation.

2. The process of claim 1 wherein the antibiotic is actaplanin.

3. The process of claim 1 wherein the antibiotic is vancomycin.

4. The process of claim 1 which employs a resin having surface area about 718 m$^2$/g and pore volume about 1.16 ml/g.

5. The process of claim 1 which empolys a resin having surface area about 650-700 m$^2$/g and pore volume about 1.4-1.5 ml/g.

6. The process of claim 1 employing a solvent comprised of 50% aqueous isopropyl alcohol acidified to about pH 1.

7. The process of claim 1 employing methanol as the polar organic solvent.

8. The process of claim 1 employing about 3% aqueous isopropyl alcohol acidified to pH 3-5.

9. The process of claim 1 employing about 3% aqueous isopropyl alcohol acidified to pH about 3.2.

* * * * *